US00PP14367P39

(12) United States Plant Patent
Friday

(10) Patent No.: US PP14,367 P3
(45) Date of Patent: Dec. 16, 2003

(54) PEACH TREE NAMED 'P.F. LUCKY 24B'

(50) Latin Name: *Prunus persica*
Varietal Denomination: P.F. Lucky 24B

(75) Inventor: Paul Jan Friday, Coloma, MI (US)

(73) Assignee: Paul J. Friday, Coloma, MI (US)

( * ) Notice: Subject to any disclaimer, the term of this patent is extended or adjusted under 35 U.S.C. 154(b) by 0 days.

(21) Appl. No.: 10/087,937

(22) Filed: Mar. 5, 2002

(65) Prior Publication Data

US 2003/0172418 P1 Sep. 11, 2003

(51) Int. Cl.[7] ..... A01H 5/00
(52) U.S. Cl. ..... Plt./198

(58) Field of Search ..... Plt./198

*Primary Examiner*—Bruce R. Campell
*Assistant Examiner*—W C Haas

(57) ABSTRACT

A new and distinct variety of peach, *Prunus persica,* tree having the following unique combination of desirable features:

1. Producing a very firm fruit that can best be described as "crunchy" when bitten into when firm ripe.
2. The limbs of the tree natura1ly grow at wide angles creating a wide-spreading tree.
3. A fruit with a smooth raised suture that remains firm as does the whole fruit.
4. A late maturing, highly colored, peach cultivar that matures a few days before the old standard variety, 'Cresthaven' (unpatented), and which hangs on the tree for many days, staying extremely firm.

1 Drawing Sheet

Botanical classification: *Prunus persica.*

ORIGIN OF VARIETY

The new peach tree (hereinafter referred to as the 'P.F. Lucky 24B' peach tree) was originated by Paul Friday in the experimental orchard, which is maintained for the purposes of breeding peach trees, at Paul Friday Farms Inc., located in Coloma, Mich. Coloma is located in the southwest section of Michigan.

In an ongoing mass selection breeding program, superior seedlings of unrecorded parentage are maintained as seed sources for the production of seeds which are collected and planted in mass. The seed producing parent trees are maintaied solely as proprietary trees for breeding purposes and have not been released from the experimental orchard, where such trees can be evaluated for their adaptability to local and regional growing conditions. Seeds resulting from open pollination of the trees in the experimental orchard are regularly planted in mass to produce new populations of seedlings which are cultured and monitored to maturity. Trees with superior attributes are retained for further observation and testing, and contribute seeds to advancing generations of new populations of seedlings.

The tree of this application, 'P.F. Lucky 24B', was a single plant from one such a seedling population, and was based on the numerous superior genetic attributes of this tree which are described in the botanical description to follow. While not comprehensive, the details of the botanical description to follow are believed to be a reasonably complete botanical description of the tree of this disclosure.

ASEXUAL REPRODUCTION OF THE VARIETY

The new and distinct variety of peach tree was asexually propagated by budding as performed in the experimental orchard of Paul Friday Farms Inc., located in Coloma, Mich. The asexual propagation demonstrates that such reproduction of the characteristics of the tree are consistent and are established and transmitted through succeeding propagation.

SUMMARY OF THE VARIETY

The new and distinct variety of peach tree is above average height and of upright growth and a regular and productive bearer of peaches. A distinct characteristic of the 'P.F. Lucky 24B' peach tree is its medium vigor having growth of about twenty-four inches (24") per year. The blossoms bloom in mid-season and are characterized by being contracted or partially spread to approximately ¾-inch when in full bloom. At the same time the five petals of the blossoms are of lesser length than the length of petals of the normal showy blossom as exemplified by the 'Loring' (unpatented) peach blossom.

The blossoms of the present peach tree at full bloom may be characterized as being non-showy. More specifically, the blossoms of the present peach tree have radially projecting and angularly spaced five blossom petals to form a blossom having a diameter of about ¾-inch measured across the blossoms.

The flesh of the fruit of the present peach tree is extremely firm and is yellow.

The skin is smooth having moderate to little down and is of dark red color overlying a yellow ground color. The yellow background covers approximately twenty percent (20%) of its surface at maturity. At maturity, the peach is spherical having an average diameter of about 2¾".

The fruit produced by this tree has firm, and non-melting flesh, and thereby has the attendant resistance to blemishes and soft spots in harvesting, shipping and handling due to bruising. The firmness of the fruit flesh is sufficient to allow the flesh to yield and be restored when bumped or dropped without the resulting soft spots as would be experienced in most late season peaches of this market class. Thus, fruit of this tree remains more attractive to the ultimate buyer, the consumer, and thereby will command premium prices for the late fresh desert market.

The fruit matures in the latter part of the peach growing season of southwestern Michigan. The fruit as mentioned heretofore is of dark red color overlying a yellow which covers approximately twenty percent (20%) of its surface and has a very attractive appearance.

BRIEF DESCRIPTION OF THE PHOTOGRAPHS

In the accompanying photographic illustrations, the top photograph shows a second generation tree in its sixth leaf (i.e., sixth year since two year grafted tree was transplanted) showing the naturally occurring wide-spreading charcteristic of this cultivar.

The bottom photograph shows two whole peaches of this cultivar depicting bright red skin color for fruit maturing so late in the season. The middle fruit has been split on a plane ninety degrees to the suture plane to depict the fruit flesh in cross section. The conformance of the pit cavity is illustrated, as is the desirable ratio of the size of the stone to the fruit size of this tree. A ruler has been placed in the photograph showing the large size of the fruit.

DESCRIPTION OF VARIETY

The detailed botanical description of the foliage and fruit of the new variety of peach tree is based upon observations of the specimens grown at Coloma, Mich. with the color terminology, other than the tenninology expressed in common terms, in accordance with the Pantone Matching System (PMS) as used internationally to identify printed colors.

Botanical classification: *Prunus persica* cultivar 'P.F. Lucky 24B'.

Tree:
- *Age.*—Six (6) years.
- *Height.*—Unpruned 13'.
- *Width.*—Unpruned 15'.
- *Size.*—Medium.
- *Vigor.*—Medium.
- *Density.*—Medium.
- *Form.*—Spreading.
- *Production.*—Very good — approximately two-thirds of the fruit must be removed annually to produce good size.
- *Bearer.*—Consistent.
- *Disease resistance to bacterial leaf and fruit spot.*—Very good.

Trunk:
- *Bark.*—Gray (417).
- *Size.*—Medium.
- *Surface.*—Medium smooth.
- *Diameter.*—4⅛"— 24" above the ground at 6 years of age.

Branches:
- *Size.*—Medium — 1 7/16" to 2⅛" at trunk union.
- *Surface.*—Medium smooth.
- *Lenticels per square inch on branch.*—Usually eight (8).
- *Lenticel color on branch.*—407.
- *Branch color.*—Gray (436).
- *Crotch angles.*—Natural wide angles — about 80 degrees.

Leaves:
- *Size.*—Average length 5¼"— average width 1⅜".
- *Form.*—Lanceolate — elongated point.
- *Thickness.*—Medium.
- *Texture.*—Smooth and shiny.
- *Margin.*—Finely rounded serrate.
- *Petiole.*—Notably short — ⅜".
- *Gland.*—Very small — usually 2 on each side of the petiole and basal portion of the leaf.
- *Gland shape.*—Elongated cup.
- *Gland color.*—Dark red.
- *Color.*—Top of leaf very dark green (357) — bottom of leaf light green (370).

Flower buds:
- *Size.*—½" long, ¼" wide.
- *Shape.*—Ovoid.
- *Color.*—218.

Flowers:
- *Blooming period.*—May 3, 2001 to May 6, 2001.
- *Size of petals.*—½" long, ¼" wide.
- *Shape of petals.*—Slightly cupped.
- *Sepal size.*—3/16" long, ⅛" wide.
- *Sepal shape.*—Cupped.
- *Sepal color.*—374.
- *Number of anthers.*—34.
- *Anther color.*—469.
- *Number of stamens.*—34.
- *Stamen length.*—⅜".
- *Stamen color.*—413.
- *Pistil length.*—5/16".
- *Pistil color.*—107.
- *Pollen.*—Present, self-fertilizing.
- *Flower and petal color.*—230.
- *Flowers per cluster.*—Usually three (3).
- *Petals per cluster.*—Five (5).
- *Fragrance.*—Very slight.

Fruit.
- *Maturity when described.*—Firm ripe.
- *Date of first picking.*—Aug. 23, 2001.
- *Date of last picking.*—Aug. 30, 2001.
- *Size.*—Large — average diameter 2¾".
- *Form.*—Oblate spherical.
- *Suture.*—Rounded but somewhat pronounced.
- *Weight.*—Average 8.3 oz.

Skin:
- *Thickness.*—Medium.
- *Texture.*—Medium.
- *Tendency to crack.*—None.
- *Down.*—Light.
- *Color.*—Light yellow ground color (113) overspread with 80% red (193) — some mottling where the colors meet.

Flesh:
- *Texture.*—Extremely firm non-melting, free of fiber.
- *Ripens.*—Evenly.
- *Flavor.*—Very good.
- *Aroma.*—Pleasant.
- *Eating quality.*—Excellent.
- *Color.*—Light yellow (100) throughout with dark red around the pit (222).

Stone:
- *Type.*—Very freestone.
- *Size.*—Average 1¼" long, 11/16" wide, ½" thick (notably small).
- *Form.*—Ovid.
- *Base.*—Straight.
- *Apex.*—Pointed.
- *Sides.*—Uneven.
- *Surface.*—Evenly furrowed.

*Color.*—Brown (478).

*Tendency to crack.*—None.

*Kernel.*—11/16" long, ½" wide, 1/16" thick.

Use: Desert.

Shipping quality: Excellent.

Keeping quality: Excellent.

The tree and its fruit herein described may vary in slight detail as a result of differences in climatic or soil conditions or cultural practices under which the tree may be grown. It is to be understood that the description of the new variety as set forth herein is that of the tree grown under the ecological conditions prevailing at Coloma, Mich.

What is claimed is:

1. A new and distinct variety of peach tree, substantially as herein illustrated and described.

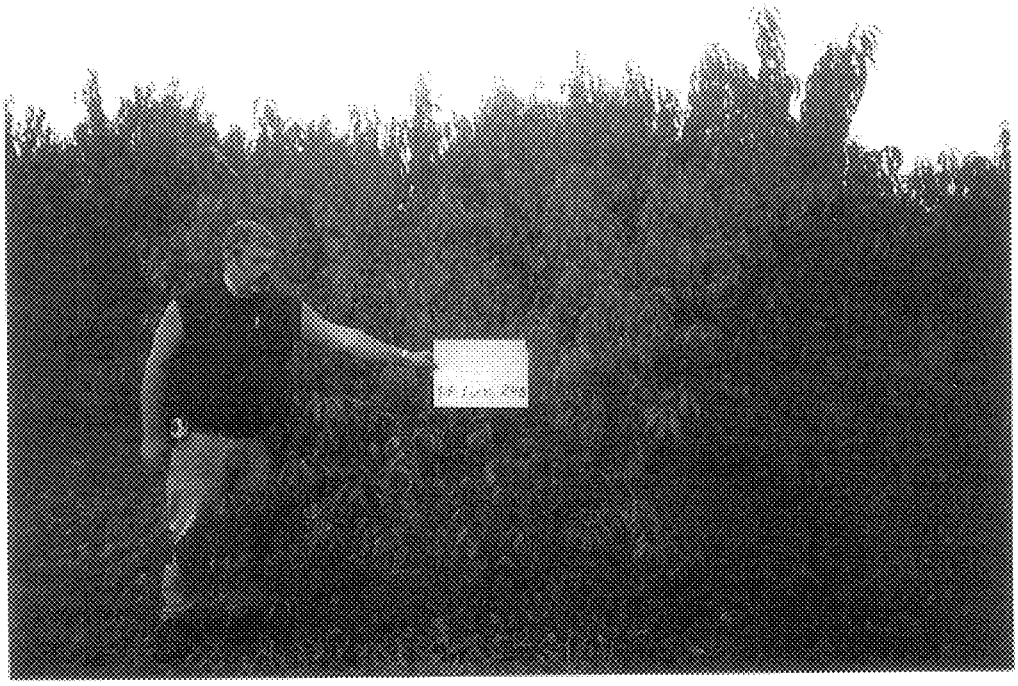
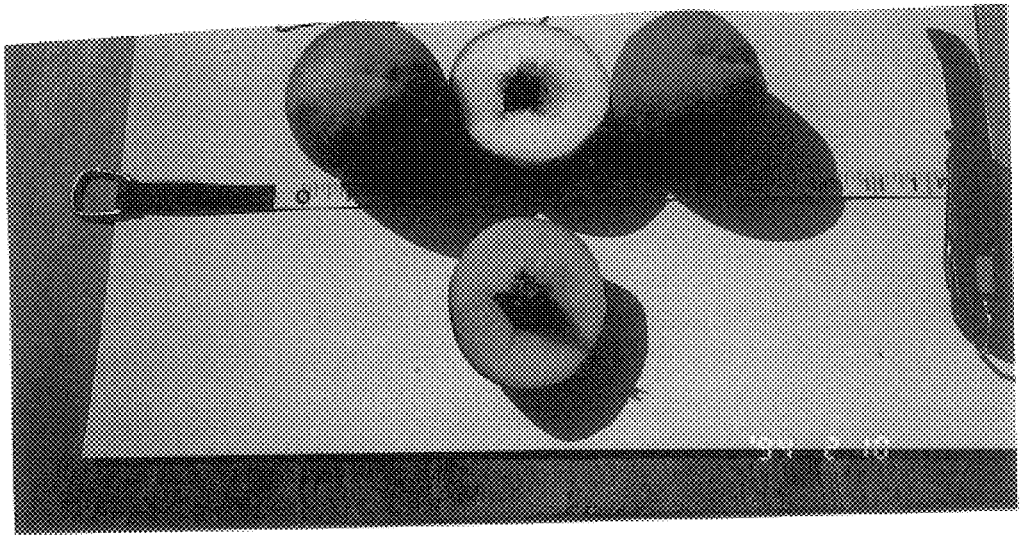

* * * * *